(12) United States Patent
Pelissier et al.

(10) Patent No.: US 10,039,527 B2
(45) Date of Patent: Aug. 7, 2018

(54) ULTRASOUND SYSTEMS INCORPORATING SPATIAL POSITION SENSORS AND ASSOCIATED METHODS

(75) Inventors: Laurent Pelissier, North Vancouver (CA); Kris Dickie, Vancouver (CA); Corina Leung, Vancouver (CA); Bo Zhuang, Richmond (CA)

(73) Assignee: Analogic Canada Corporation, Sainte-Laurent (CA)

( * ) Notice: Subject to any disclaimer, the term of this patent is extended or adjusted under 35 U.S.C. 154(b) by 1926 days.

(21) Appl. No.: 12/703,706

(22) Filed: Feb. 10, 2010

(65) Prior Publication Data
US 2010/0298712 A1  Nov. 25, 2010

Related U.S. Application Data

(60) Provisional application No. 61/180,050, filed on May 20, 2009.

(51) Int. Cl.
*A61B 8/00* (2006.01)
*A61B 8/08* (2006.01)

(52) U.S. Cl.
CPC .............. *A61B 8/58* (2013.01); *A61B 8/0833* (2013.01); *A61B 8/0841* (2013.01); *A61B 8/4245* (2013.01); *A61B 8/4263* (2013.01); *A61B 8/463* (2013.01)

(58) Field of Classification Search
USPC .................................. 600/407, 424, 437, 459
See application file for complete search history.

(56) References Cited

U.S. PATENT DOCUMENTS

| 4,173,228 A | 11/1979 | Van Steenwyk et al. |
| 4,567,896 A | 2/1986 | Barnea et al. |
| 4,905,698 A | 3/1990 | Strohl, Jr. et al. |

(Continued)

FOREIGN PATENT DOCUMENTS

| WO | 1996031753 A2 | 10/1996 |
| WO | 9958055 A1 | 11/1999 |

(Continued)

OTHER PUBLICATIONS

Hsu, P-W et al., "Freehand 3D Ultrasound Calibration: A Review", CUED/F-INFENG/TR 584, University of Cambridge Department of Engineering, Dec. 2007.

(Continued)

*Primary Examiner* — Tse Chen
*Assistant Examiner* — Jason Ip
(74) *Attorney, Agent, or Firm* — Anthony M. Del Zoppo, III; Driggs, Hogg, Daugherty & Del Zoppo, Co., LPA

(57) ABSTRACT

An ultrasound probe is equipped with a transducer element array and an internally located position marker trackable by a position sensing system or the like. The position marker is supported by a movement and rotation constraining fixture. The fixture is rigidly connected to the transducer element array of the probe. The fixture constrains the position and orientation of the position marker to match a spatial reference relationship with the transducer element array in the position marker's constrained degrees of freedom. The position marker may moved along and rotated in its unconstrained degrees of freedom to match the spatial reference relationship with the transducer element array.

18 Claims, 4 Drawing Sheets

(56) References Cited

U.S. PATENT DOCUMENTS

| | | | |
|---|---|---|---|
| 5,078,140 A | 1/1992 | Kwoh | |
| 5,095,910 A | 3/1992 | Powers | |
| 5,211,165 A | 5/1993 | Dumoulin et al. | |
| 5,425,367 A | 6/1995 | Shapiro et al. | |
| 5,443,489 A | 8/1995 | Ben-Haim | |
| 5,515,853 A | 5/1996 | Smith et al. | |
| 5,638,819 A | 6/1997 | Manwaring | |
| 5,647,373 A | 7/1997 | Paltieli | |
| 5,771,896 A | 6/1998 | Sliwa, Jr. et al. | |
| 5,797,849 A | 8/1998 | Vesely et al. | |
| 5,868,675 A | 2/1999 | Henrion et al. | |
| 6,122,538 A | 9/2000 | Sliwa, Jr. et al. | |
| 6,138,495 A | 10/2000 | Paltieli et al. | |
| 6,203,497 B1 | 3/2001 | Dekel et al. | |
| 6,338,716 B1 | 1/2002 | Hossack et al. | |
| 6,459,925 B1 | 10/2002 | Nields et al. | |
| 6,517,491 B1 | 2/2003 | Thiele et al. | |
| 6,524,247 B2 | 2/2003 | Zhao et al. | |
| 6,558,333 B2 | 5/2003 | Gilboa et al. | |
| 6,628,977 B2 | 9/2003 | Graumann et al. | |
| 6,733,458 B1 | 5/2004 | Steins et al. | |
| 6,764,449 B2 | 7/2004 | Lee et al. | |
| 6,875,179 B2 | 4/2005 | Ferguson et al. | |
| 7,142,905 B2 | 11/2006 | Slayton et al. | |
| 7,174,202 B2 | 2/2007 | Bladen et al. | |
| 7,184,991 B1 | 2/2007 | Wentland et al. | |
| 7,244,234 B2 | 7/2007 | Ridley et al. | |
| 7,366,562 B2 | 4/2008 | Dukesherer et al. | |
| 7,383,237 B2 | 6/2008 | Zhang et al. | |
| 7,496,398 B2 | 2/2009 | Nields et al. | |
| 7,510,536 B2 | 3/2009 | Foley et al. | |
| 7,529,393 B2 | 5/2009 | Peszynski et al. | |
| RE40,852 E | 7/2009 | Martinelli et al. | |
| 7,599,730 B2 | 10/2009 | Hunter et al. | |
| RE41,066 E | 12/2009 | Martinelli et al. | |
| 7,751,868 B2 | 7/2010 | Glossop | |
| 2002/0156376 A1 | 10/2002 | Wang et al. | |
| 2003/0013959 A1 | 1/2003 | Grunwald et al. | |
| 2003/0073895 A1 | 4/2003 | Nields et al. | |
| 2003/0210812 A1 | 11/2003 | Khamene et al. | |
| 2004/0097806 A1 | 5/2004 | Hunter et al. | |
| 2004/0106869 A1 | 6/2004 | Tepper | |
| 2004/0109608 A1 | 6/2004 | Love et al. | |
| 2004/0210547 A1 | 10/2004 | Wentland et al. | |
| 2005/0085793 A1 | 4/2005 | Glossop | |
| 2005/0182295 A1 | 8/2005 | Soper et al. | |
| 2006/0184016 A1 | 8/2006 | Glossop | |
| 2006/0241577 A1 | 10/2006 | Balbierz et al. | |
| 2007/0167801 A1 | 7/2007 | Webler et al. | |
| 2007/0197896 A1 | 8/2007 | Moll et al. | |
| 2007/0232882 A1 | 10/2007 | Glossop et al. | |
| 2008/0132785 A1 | 6/2008 | Piron et al. | |
| 2008/0132911 A1 | 6/2008 | Sobe | |
| 2008/0159653 A1* | 7/2008 | Dunki-Jacobs et al. | 382/293 |
| 2008/0183071 A1 | 7/2008 | Strommer et al. | |
| 2008/0287787 A1 | 11/2008 | Sauer et al. | |
| 2009/0069679 A1 | 3/2009 | Hibi | |
| 2009/0143674 A1 | 6/2009 | Nields et al. | |
| 2009/0221908 A1 | 9/2009 | Glossop | |
| 2009/0274357 A1 | 11/2009 | Wilson et al. | |
| 2010/0298704 A1 | 11/2010 | Pelissier et al. | |

FOREIGN PATENT DOCUMENTS

| | | |
|---|---|---|
| WO | 2004019799 A1 | 3/2004 |
| WO | 2004023103 A1 | 3/2004 |
| WO | 2007027511 A2 | 3/2007 |
| WO | 2007067323 A2 | 6/2007 |
| WO | 2009049082 A1 | 4/2009 |
| WO | 2009153723 A1 | 12/2009 |

OTHER PUBLICATIONS

Krucker, J. et al., "Electromagnetic Tracking for Thermal Ablation and Biopsy Guidance: Clinical Evaluation of Spatial Accuracy", J Vasc Interv Radiol. Sep. 2007; 18(9): 1141-1150.

Nagel, M. et al., "Electromagnetic Tracking System for Minimal Invasive Interventions Using a C-arm System with CT Option: First Clinical Results", Medical Imaging 2008: Visualization, Image-guided Procedures, and Modeling, Proc. of SPIE, vol. 6918 (2008).

Leotta, D. F. et al., "Performance of a Miniature Magnetic Position Sensor for Three-Dimensional Ultrasound Imaging", Ultrasound in Med. & Biol., vol. 23, No. 4, pp. 597-669, 1997.

* cited by examiner

ULTRASOUND SYSTEMS INCORPORATING SPATIAL POSITION SENSORS AND ASSOCIATED METHODS

REFERENCE TO RELATED APPLICATION

The present application claims the benefit, under 35 U.S.C. § 119(e), of U.S. Provisional Application Ser. No. 61/180,050 filed 20 May 2009 entitled "Ultrasound systems incorporating spatial position sensors and associated methods" which is incorporated herein by this reference.

TECHNICAL FIELD

This invention relates to ultrasound imaging. The invention has particular application in the field of medical ultrasonography and oncology.

BACKGROUND

Ultrasound imaging is widely used in a range of medical applications. One area in which ultrasound imaging is used is to guide biopsy procedures. A biopsy typically involves identifying an abnormality of interest, such as suspicious solid mass, a distortion in the structure of a body tissue, or an area of abnormal tissue change. A needle or other fine member may be inserted into the abnormality and used to withdraw a small tissue sample for investigation.

A problem with the use of ultrasound to guide a needle or wire in any of these procedures, or like procedures, is that it may be difficult to determine the spatial relationship between the ultrasound image and the needle or wire. In particular, it may be difficult to determine the relationship between the scan plane of an ultrasound image and a needle or other fine member when the needle or other fine members is out of the plane of the ultrasound image.

A similar problem arises when using images acquired by a freehand ultrasound probe to construct a 3D model of a body. In order form a 3D model of a body as a composite of image data from multiple images corresponding to different scan planes, the locations of the scan planes relative to one another must be known. As the probe is moved, the ultrasound scan plane moves and the region of the body imaged by the probe changes.

The following US patents and publications disclose technology that may be in the general field of this invention:
US 2009/0221908 A1, Glossop
U.S. Pat. No. 6,138,495, Paltieli et al.
U.S. Pat. No. 6,122,538, Sliwa et al.
U.S. Pat. No. 6,338,716, Hossack et al.
U.S. Pat. No. 5,771,896, Sliwa et al.
U.S. Pat. No. 6,517,491, Thiele et al.
*Freehand 3D Ultrasound Calibration: A Review*, P-W. Hsu, R. W. Prager A. H. Gee and G. M. Treece CUED/F-INFENG/TR 584, University of Cambridge Department of Engineering, December 2007

SUMMARY

One aspect of the invention provides a trackable ultrasound probe for use in acquiring ultrasound data. In some embodiments according to this aspect, the probe comprises a transducer element array for acquiring the ultrasound image; a mount supporting the transducer element array at a fixed location and orientation; a position marker whose location and orientation is trackable relative to a reference coordinate system by a position sensing system; and a fixture rigidly connected to the mount, the fixture supporting the position marker and configured to substantially constrain rotation of the position marker in two degrees of rotational freedom and configured to substantially constrain translational displacement of the position marker along two degrees of translational freedom. In some such embodiments, the orientation of the position marker in the two degrees of rotational freedom determined by the fixture and the location of the position marker along the two degrees of translational freedom determined by the fixture correspond to a pre-determined reference relationship relative to the transducer element array.

In some other embodiments according to this aspect, the probe comprises a housing; a transducer element array for acquiring ultrasound data, the transducer element array supported at a fixed location and orientation in the housing; a recess defined in the housing and having an end at a pre-determined distance from the transducer element array; and a position marker trackable relative to a reference coordinate system by a position sensing system. In some such embodiments the position marker is snugly fitted in the recess, such that an axis by which the orientation of the position marker is measured is aligned with an axis of the recess, thereby determining two orientation angles of the position marker.

Another aspect of the invention provides apparatus for mounting a position marker to an ultrasound probe having a fixture configured to substantially limit rotation of the position marker to rotation about a rotational axis and configured to substantially limit translational displacement of the position marker to translational displacement along a translational axis. In some embodiments according to this aspect, the apparatus comprises a jig having a seat for supporting the ultrasound probe; a position base unit mounted on the jig, the position base unit configured to determine a real-time location and orientation of the position marker with respect to first, second and third orthogonal reference axes; and a real-time display comprising an indication of the real-time location and orientation of the marker determined by the position base unit. In some such embodiments, the seat is configured to support the probe such that the rotational axis and at least one of the first, second and third reference axes are in alignment and such that the translational axis and at least one of the first, second and third reference axes are in alignment.

A further aspect of the invention provides a method for installing a position marker in an ultrasound probe at a desired spatial relationship with an ultrasound transducer element array of the probe, the ultrasound probe comprising a fixture configured to substantially limit rotation of the position marker to rotation about a rotational axis and configured to substantially limit translational displacement of the position marker to translational displacement along a translational axis. In embodiments according to this aspect, the method comprises: positioning the probe in a pre-determined spatial relationship with a position base unit, the position base unit configured to determine a real-time location and orientation of the marker; positioning the position marker in the fixture, thereby determining the location of the position marker along axes orthogonal to the translational axis and determining the orientation of the position marker about axes orthogonal to the rotational axis; displacing the position marker along the translational axis to a location whereat the real-time location of the position marker determined by the position base unit matches a pre-determined position corresponding to the desired spatial relationship; and rotating the position marker about the rotational axis to an orientation whereat the real-time orientation of the position marker determined by the position base unit matches a pre-determined orientation corresponding to the desired spatial relationship.

Yet another aspect of the invention provides apparatus for calibrating a position marker in an ultrasound probe, the apparatus comprising a jig having a seat for supporting the ultrasound probe, a position base unit mounted on the jig, the position base unit configured to determine a real-time location and orientation of the position marker with respect to first, second and third reference axes, and a real-time display comprising an indication of the real-time location and orientation of the marker determined by the position base unit, wherein the seat is configured to support the probe in a predetermined position and orientation relative to the position base unit. In some embodiments according to this aspect, the seat comprises a surface that conforms to contours of the exterior of the probe.

Further aspects of the invention and features of the example embodiments of the invention are described below and depicted in the accompanying drawings.

BRIEF DESCRIPTION OF DRAWINGS

The accompanying drawings illustrate non-limiting embodiments.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
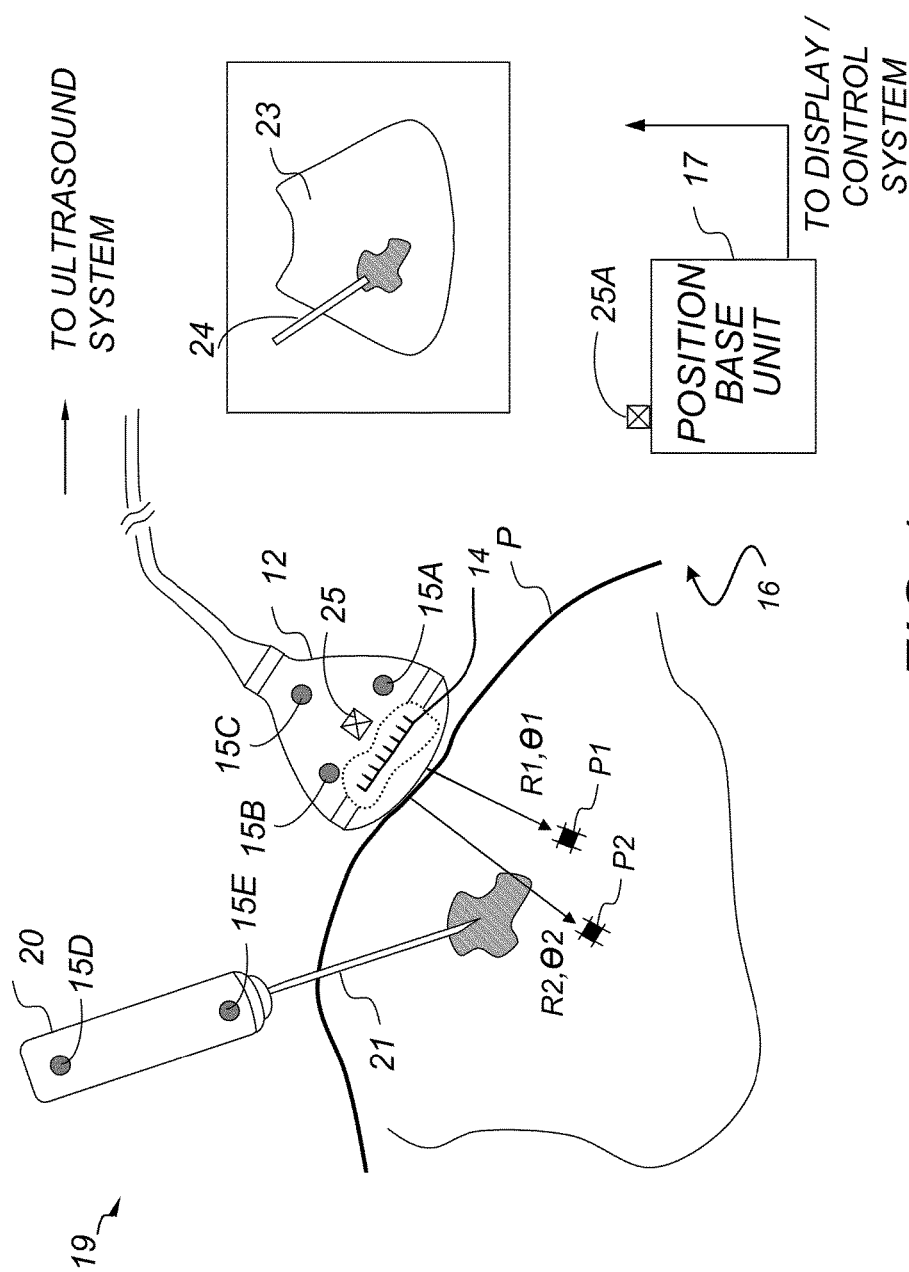
FIG. 1 is a schematic depiction of an example ultrasound probe and biopsy assembly as may be used with the invention.

FIG. 1 shows an ultrasound probe 12. Probe 12 comprises a transducer element array 14 that can generate high frequency vibrations and transmit those high frequency vibrations into the body of a patient P. The vibrations are reflected from various structures and interfaces within patient P. Reflected signals are detected at transducer element array 14 where they are converted to electronic form and delivered to an ultrasound system (not shown in FIG. 1) for further analysis. Transducer element array 14 may comprise a one or two-dimensional array of transducer elements, for example. The particular arrangement of transducer elements in array 14 may be selected based upon the medical application for which the probe 12 will be used.

To create a diagnostic image, an ultrasound controller causes electrical excitation signals to be delivered to elements of transducer element array 14. The transducer elements convert the excitation signals into ultrasonic vibrations. The ultrasonic vibrations typically have frequencies in the range of about 2 megahertz to about 15 megahertz. This is not mandatory. Embodiments may employ frequencies outside of this range.

The ultrasonic vibrations are scattered and/or reflected by various structures in the patient's body. Some of the reflected and/or scattered ultrasonic vibrations, which may be called echos, are received at transducer element array 14. The distance from the transducer element array 14 to a particular location at which echos are generated may be determined by the time between the transmission of an ultrasonic vibration and the receipt of an echo of that ultrasonic vibration at transducer element array 14. The direction relative to probe 12 of a location at which an echo is generated may be determined by processing the echo signals. Various beam forming techniques may be used to determine the directions from which echos arrive at transducer element array 14.

For example, in so-called B-mode imaging, a 2D image of a selected cross-section of the patient's body is generated. Because the location and orientation of transducer element array 14 is fixed in probe 12, the particular cross section represented by an ultrasound image depends upon the current location and orientation of probe 12 relative to the patient's body. Moving probe 12 relative to the patient's body will result in a different cross section being imaged.

FIG. 1 shows two scattering locations, P1 and P2. P1 is located at position R1, θ1. P2 is at location R2, θ2. These locations are both determined with reference to a coordinate system that can be considered to be attached to probe 12.

The location and orientation of probe 12 are monitored by a 3D position sensor system 16. The 3D position sensor system 16 may include one or more base units and one or more markers carried on probe 12. In the illustrated embodiment, probe 12 includes a plurality of position markers 15. In the illustrated embodiment, there are three position markers, 15A, 15B, and 15C. Position markers 15A, 15B, and 15C are not located along a common line. Therefore, if the locations of position markers 15A, 15B, and 15C are known, the location and orientation in space of probe 12 is uniquely determined. Since the particular cross section represented by an ultrasound image depends upon the current location and orientation of probe 12, the location and orientation of ultrasound images can be determined from the location and orientation in space of probe 12.

The positions of location markers 15 relative to a global coordinate system are measured by 3D position sensor system 16. In the illustrated embodiment sensor system 16 includes a position base unit 17. 3D position base unit 17 and position markers 15 may comprise any suitable technology. For example, 3D position base unit 17 may detect electromagnetic or other fields emitted by position markers 15 or vice versa. In some embodiments the position base unit 17 generates a magnetic field that is sensed by position markers 15. A 3D position sensing system may, for example, comprise a medSAFE™ or drive BAY™ position sensor available from Ascension Technology corporation of Burlington, Vt., USA.

Some 3D position sensing technologies permit the location and/or orientation of a single position marker to be determined for multiple degrees of freedom. Position sensing technologies may determine any combination of the six degrees of freedom (translation up/down (heaving), translation left/right (swaying), translation forward/backward (surging), tilting forward/backward (pitching), turning left/right (yawing), tilting side to side (rolling)) for a single position marker. For example, a six-degree-of-freedom position marker may have its location and orientation determined in all six degrees-of-freedom. In embodiments where position sensing technologies permit multiple degrees of freedom to be determined for position markers, fewer position markers 15 are required to determine the location and orientation of probe 12 than would be the case for position markers for which only one degree of freedom is determined.

Even in embodiments which detect the orientations of position markers, some redundant position markers 15 may be provided. In embodiments which provide more position markers than are required to identify location and orientation of probe 12, positions of the additional position markers may be monitored by 3D position base unit 17 and used to provide information regarding the location and orientation of probe 12 of enhanced accuracy.

FIG. 1 also shows a biopsy apparatus 19 which includes a handle 20 and a needle 21. Biopsy apparatus 19 includes one or more position markers 15. In the illustrated embodiment, there are two position markers 15, individually identified as 15D and 15E. In the illustrated embodiment, position markers 15D and 15E are located so that they correspond to reference locations on an extension of a longitudinal axis of needle 21. Neglecting rotations about the axis of needle 21, the location and orientation of needle 21 can be uniquely determined if the locations of position markers 15D and 15E are known. In the illustrated embodiment, the locations of position markers 15D and 15E are monitored by 3D position sensor system 16.

In an alternative embodiment, biopsy apparatus 19 has one position marker of a type such that position base unit 17 can determine both a location and orientation of the position marker. The one position marker may, for example, comprise a six degrees of freedom marker. Additional position markers may optionally be provided on biopsy apparatus 19.

In the illustrated embodiment, position markers 15D and 15E are built into a handle of biopsy apparatus 19. Needle 21 is detachably affixable to the handle.

It can be appreciated that the apparatus illustrated in FIG. 1 may facilitate the placing of needle 21 into the body of patient P such that needle 21 may be used to acquire a tissue sample or place something at a desired location within patient P. Specifically, when an ultrasound image 23 is generated from ultrasound data acquired by probe 12, the precise location and orientation of needle 21 relative to that ultrasound image can be determined from the known locations of position markers 15 on probe 12 and biopsy assembly 19. Having this information allows the location of needle 21 to be illustrated clearly on image 23 (even if the ultrasound echos do not provide a clear image of needle 21). In the illustrated embodiment, needle 21 is represented by a computer-generated line 24 that shows the position of needle 21 in image 23, as calculated based on the relative positions of position markers 15.

Knowledge of the relative orientations of probe 12 and needle 21 also permits the generation of other views which help the user to visualize the location of needle 21 relative to its intended target 25 or 25A. For example, in some embodiments, a display displays both an image taken in the current image 5 plane of transducer 12 and one or more virtual depictions of a needle intersecting a 3D volume as the needle is tracked.

Because location and orientation information from position markers on probe 12 indicates the position of the markers in 3D space, locating the ultrasound image (scan plane) in 3D space requires determining the relationship between the location and orientation of the ultrasound image and the markers on probe 12. Various methods for calibrating freehand ultrasound probes that may be applied to establish a correspondence between points in an ultrasound image obtained using probe 12 and corresponding points in a global coordinate system are described in *Freehand 3D Ultrasound Calibration: A Review*, P-W. Hsu, R. W. Prager A. H. Gee and G. M. Treece CUED/F-INFENG/TR 584, University of Cambridge Department of Engineering, December 2007 which is hereby incorporated herein by reference.

Previously, position markers have been located externally on probes and needles. Advantageously, embodiments provide for position markers installed in the probe housing and/or needle body. Such internally located position markers may be installed during manufacture of the probe. In some embodiments, internally located position markers are installed in a probe housing in a known spatial relationship with the transducer element(s) of the probe. For example, both position markers and transducer elements may be installed in a chassis that fixes the relative positions and orientations of the position markers and transducer elements. Such a chassis may form part of, be integral with, or be rigidly connected to, the probe housing. In some embodiments, a chassis is a unitary piece. A chassis may comprise means for adjusting the location and/or orientation of positions markers, transducer elements or both, such as, for example, set screws, an adjustable carriage or the like.

In embodiments where the relative locations and/or orientations of internally mounted position markers and/or transducer elements may be adjusted, calibration may be performed during probe manufacture. Probes according to such embodiments may comprise housings that prevent external access to the means for adjusting the relative locations and/or orientations of the position markers and/or transducer elements. It will be understood that with probes of this construction, the relative location and orientation of position markers and transducer elements may be insulated from disturbance by external forces.

Probes may also comprise means for permanently fixing the relative locations and/or orientations of the position markers and/or transducer elements after initial calibration, such a for example, glue or the like. Such probes may include unitary protective casings that envelope position markers and transducer elements so as to inhibit relative motion therebetween. For example, a casing enclosing position markers and transducer elements may be filled with resin which hardens into a substantially incompressible casing.

In other embodiments, means for adjusting the relative locations and/or orientations of position markers and transducer elements are manipulable from outside the probe housing. Such adjustment means may be insulated from inadvertent or accidental manipulations, such as, for example, by covers, sunken installation, or the like.

In some applications, it is desirable that the probes can be interchanged without having to perform calibration. Advantageously, embodiments provide sets of probes which have position markers that are identically situated with respect to the transducer element array of each of the probes. Uniform relative positioning of position markers and transducer element arrays may be facilitated during probe assembly. For example, position markers may be placed in different probes in a common reference relationship with respect to the transducer element arrays of those probes, the reference relationship characterized by the same displacement from the transducer element arrays (e.g., for position markers that provide information in translational degrees of freedom) and/or orientation with respect to the transducer element arrays (e.g., for position markers that provide information in rotational degrees of freedom). In some embodiments, the reference relationship is maintained by the alignment of one or more position marker orientations with the axes, lines and/or planes of symmetry of the ultrasound transducer element array (i.e., axes, lines and/or planes of symmetry of physical objects that correspond to axes, lines and/or planes of symmetry of the ultrasound image plane or space).

Some embodiments provide probes that comprise memories. In some such embodiments, calibration information is stored in the memories. Calibration information may comprise, for example, translational and/or angular offsets that establish a correspondence between points in ultrasound images obtained using the probe and corresponding points in a global coordinate system by which the location and orientation of the probe is determined. Calibration information may be stored in the memories at the time of probes manufacture. In some embodiments, calibration information may be refreshed using calibration information obtained during a post-manufacture calibration procedure. Probes may be provided with connectors for communicating calibration information to ultrasound imaging apparatus, position sensing systems, or the like. Where calibration information is communicated to an ultrasound imaging apparatus, a probe may be connected to the apparatus and used without having to perform calibration.

Figure 2:
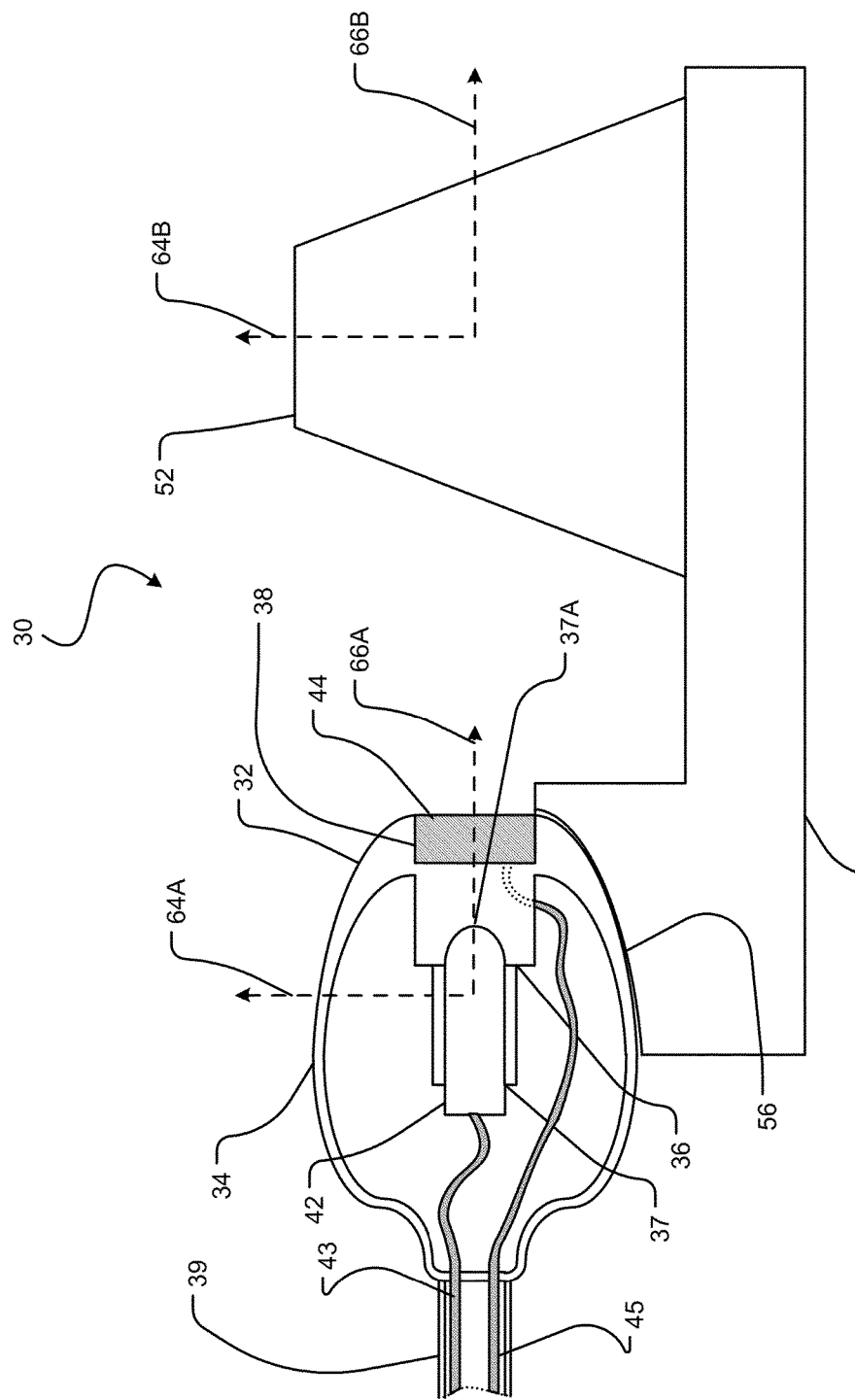
FIG. 2 is a side elevation cross-sectional view of a marker positioning apparatus according to an example embodiment.
Figure 3:
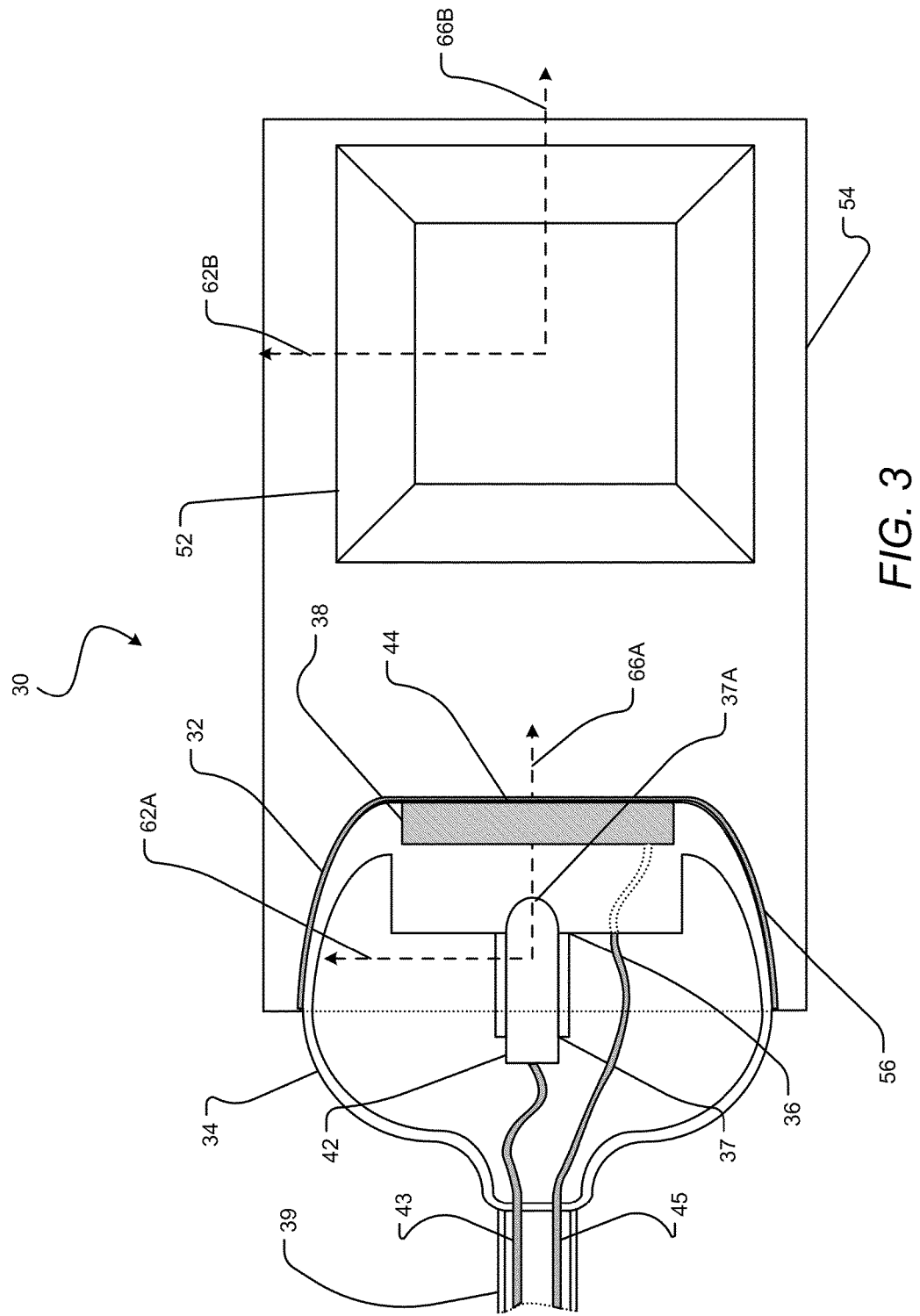
FIG. 3 is a top plan cross-sectional view of a marker positioning apparatus according to an example embodiment.

FIG. 2 shows a side elevation cross-sectional view of an example embodiment of a marker positioning apparatus 30 that may be used for mounting a position marker 42 in a probe 32 in a reference relationship with a transducer element array 44. FIG. 3 shows a top cross-sectional view of positioning apparatus 30. Probe 32 comprises a housing 34 having a position marker constraining fixture 36. Fixture 36 comprises a recess 37. In the particular illustrated embodiment, recess 37 comprises a cylindrical bore. Fixture 36 constrains rotation of position marker 42 in two degrees of rotational freedom, i.e., about axes 62A and 64A. Fixture 36 thus determines the orientation of position marker 42 in those two degrees of rotational freedom and limits rotation of position marker 42 to one degree of rotational freedom, i.e., rotation about axis 66A. Fixture 36 constrains translational displacement of position marker 42 along two degrees of translational freedom, i.e., along axes 62A and 64A. Fixture 36 thus determines the location of position marker 42 along those two degrees of translational freedom and limits translational displacement of position marker 42 to one degree of translational freedom, i.e., translational displacement along axis 66A. Fixture 36 and position marker 42 are configured such that the axes of rotational and translational freedom are coincident (i.e., about and along axis 66A). Coincidence of axes of rotational and translational degrees of freedom is not necessary in other embodiments.

Housing 34 also comprises a mount 38, which in the illustrated embodiment comprises a recess formed in housing 34, configured for complementary fitting with a transducer element array 44. When transducer element array 44 is installed in mount 38, it is supported by mount 38 at a fixed location and orientation. Fixture 36 and mount 38 are rigidly connected so that the spatial relationship between fixture 36 and mount 38 is fixed. As a result, the location and orientation of position marker 42 with respect to transducer element array 44 is determined by fixture 36 but for one degree of translational freedom and one degree of rotational freedom. Housing 34, fixture 36 and mount 38 are configured so that when position marker 42 is installed in fixture 36 and transducer element array 44 is installed in mount 38, the spatial relationship between position marker 42 and transducer element array 44 corresponds to the reference relationship in all but the free degrees of freedom permitted to position marker 42 by fixture 36. In other words, the configuration of mount 38, the rigid connection of mount 38 to fixture 36, and the constraints on freedom of rotational and translation provided by fixture 36 combine to determine the orientation and location of position marker 42 relative to transducer element array 44 such that the orientation and location of position marker 42 in the constrained degrees of freedom corresponds to the reference relationship.

Position marker 42 can be positioned translationally and rotationally along its free degrees of freedom to a location and orientation with respect to transducer element array 44 that corresponds to the reference relationship. The constraints on the freedom of movement and rotation of position marker 42 provided by fixture 36 may assist placement of position marker 42 in the reference relationship with transducer element array 44. Since installing position marker 42 in fixture 36 results in the spatial relationship between position marker 42 and transducer element array 44 meeting the reference relationship in all but the free degrees of freedom of position marker 42, placing position marker 42 in the reference relationship requires only translation along the one degree of translational freedom permitted by fixture 36 and rotation about the one degree of rotational freedom permitted by fixture 36.

It will be appreciated that embodiments may provide fixtures that constrain any number of degrees of freedom of position markers. In some embodiments, probes comprise one or more fixture-position marker pairs in which all degrees of translational and rotational freedom of the position marker are constrained by the fixture. In some such embodiments, the fixtures comprise a plurality of pieces that are assembled after the position markers are installed. In some embodiments, probes comprise one or more fixture-position marker pairs in which all degrees of translational freedom of the position marker are constrained by the fixture and not all degrees of rotational freedom of the position marker are constrained by the fixture. In some embodiments, probes comprise one or more fixture-position marker pairs in which all degrees of rotational freedom of the position marker are constrained by the fixture and not all degrees of translational freedom of the position marker are constrained by the fixture.

As shown in FIGS. 2 and 3, in the illustrated embodiment:
housing 34 is reflectively symmetric about a plane defined by axes 64A and 66A and about a plane defined by axes 62A and 66A;
fixture 36 is rotationally symmetric about axis 66A;
fixture 36 is reflectively symmetric about the plane defined by axes 62A and 66A and about the plane defined by axes 64A and 66A;
mount 38 is reflectively symmetric about the plane defined by axes 62A and 66A and about the plane defined by axes 64A and 66A;
position marker 42 is rotationally symmetric about axis 66A;
position marker 42 is reflectively symmetric about the plane defined by axes 62A and 66A and about the plane defined by axes 64A and 66A; and
transducer element array 44 is reflectively symmetric about the plane defined by axes 62A and 66A and about the plane defined by axes 64A and 66A.

It is thus apparent that:
fixture 36 is located on a line of intersection of two planes of symmetry of housing 34;
fixture 36 is rotationally symmetric about a line of intersection of two planes of symmetry of housing 34;

fixture 36 is reflectively symmetric about two planes of symmetry of housing 34;

mount 38 is located on a line of intersection of two planes of symmetry of housing 34;

mount 38 reflectively symmetric about two planes of symmetry of housing 34;

fixture 36 and mount 38 have two common planes of symmetry;

position marker 42 and transducer element array 44 have two common planes of symmetry;

the axis of the free degree of rotational freedom of position marker 42 lies along a line of intersection of two planes of symmetry of housing 34;

the axis of the free degree of rotational freedom of position marker 42 lies along a line of intersection of two planes of symmetry of transducer element array 44;

the axis of the free degree of translational freedom of position marker 42 lies along a line of intersection of two planes of symmetry of housing 34; and the axis of the free degree of translational freedom of position marker 42 lies along a line of intersection of two planes of symmetry of transducer element array 44.

In some embodiments, fixture 36 is reflectively symmetric about a single plane of symmetry of housing 34 and/or mount 38. In some embodiments, the axis of the free degree of rotational freedom of position marker 42 lies in a single plane of symmetry of housing 34, mount 38 and/or transducer array 44. In some embodiments, fixture 36 and/or position marker 42 do not share any axes and/or planes of symmetry in common with housing 34, mount 38 and/or transducer array 44.

In some embodiments, an axis about which rotation of position marker 42 is measured: is in a plane into which transducer element array 44 emits ultrasound beams; and/or passes through a central element of transducer element array 44. In some embodiments transducer element array 44 emits acoustic radiation in a forward direction and position marker 42 is directly behind transducer element array 44 in a direction opposed to the forward direction.

Position base unit 52 provides location and orientation information for position marker 42 relative to reference axes 62B, 64B and 66B. Probe 32 and position base unit 52 are mounted on a jig 54. In some embodiments, the distance between probe 32 and position base unit 52 is in the range of 8 and 40 cm. Jig 54 comprises a seat 56 that conforms to a portion of the exterior of housing 34. Because housing 34 is rigid, the spatial relationship between mount 38 and the portion of housing 34 that fits seat 56 is fixed. As a result, mounting of probe 32 and position base unit 52 on jig 54 determines the location and orientation of transducer element array 44, which is fitted in mount 38, with respect to position base unit 52. A reference relationship for position marker 42 and transducer element array 44 can thus be specified in terms of a location (e.g., X, Y, Z coordinate) and/or an orientation (e.g., azimuth, elevation and rotation angles) of position marker 42 measured by position base unit 52.

Signal connectors 43 and 45 exit probe 32 inside sleeve 39. Signal connectors 43 and 45 carry position sensing information and ultrasound data, respectively, from position marker 42 and transducer element array 44, respectively. Signal connector 43 has a connection (not shown) to position base unit 52, by which position base unit may receive position sensing information from position marker 42.

In order that position markers can be positioned uniformly with respect to the transducer arrays of different probes, mounting a probe in jig 54 should result in substantially the same spatial relationship between the transducer element array of the probe and position base unit 52. Seat 56 ensures that all probes of the same model as probe 32 will be identically mounted in jig 54. As a result, the location and orientation of the transducer element arrays of such probes with respect to position base unit 52 will be the same as the position and orientation of transducer element array 44.

Figure 4:
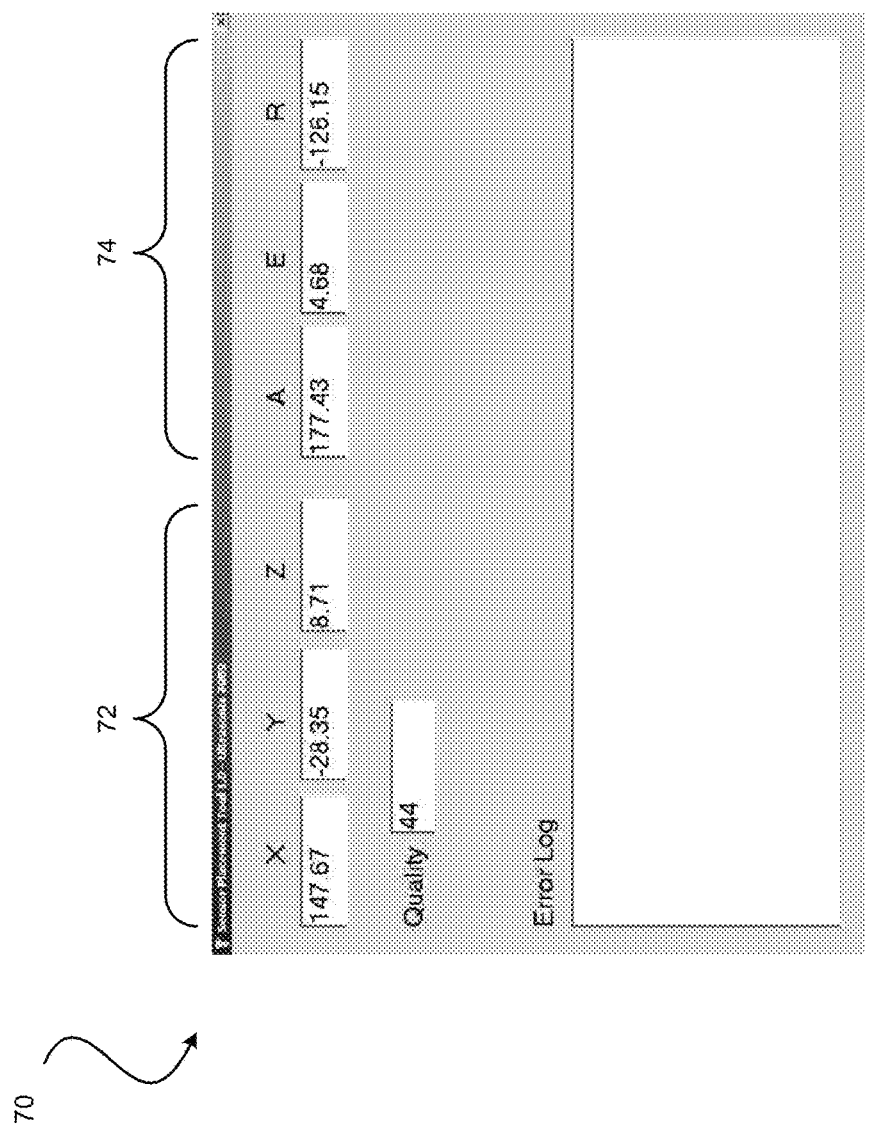
FIG. 4 is a real-time display of marker location and orientation according to an example embodiment.

In some embodiments, a real-time display of the location and/or orientation of position marker 42, as determined by position base unit 52, is provided to a user. FIG. 4 is a screen-capture of an example real-time display 70 of the location 72 and orientation 74 of a marker according to an example embodiment. A user can use real-time location and orientation information to guide the placement of position marker 42 into a reference relationship characterized by a reference location (e.g., X, Y, Z coordinate) and/or a reference orientation (e.g., azimuth, elevation and rotation angles) with respect to position base unit 52.

After position marker 42 has been positioned in fixture 36 at the location and orientation corresponding to the reference relationship, it's placement in fixture 36 can be fixed by the application of an adhesive, resin or the like.

Fixture 36 comprises end 37A, which provides an endpoint to the translational freedom of position marker 42. Fixture 36 and housing 34 may be configured such that when position sensor 42 abuts end 37A, the location of position sensor 42 relative to transducer element array 44 corresponds to the reference relationship in all translational degrees of freedom. Embodiments comprising this configuration permit a user to locate and orient position marker 42 in substantial correspondence with the reference relationship in all but the free degree of rotational freedom permitted by fixture 36 merely by abutting marker 42 against end 37A.

In some embodiments, fixture 36 may provide an endpoint to the translational freedom of position marker 42 at which position marker 42 is nearer to transducer element array 44 than the reference relationship. In such embodiments, a spacer may be deposited in abutment with the endpoint in order to increase the minimum separation between position marker 42 and transducer element array 44. The location of the translational freedom endpoint provided by fixture 36 may be ascertained and a spacer of a pre-determined dimension placed in abutment with the endpoint to set the minimum separation between position marker 42 and transducer element array 44 at a desired distance. For example, a spacer could be placed to set the minimum separation between position marker 42 and transducer element array 44 at a distance corresponding to the reference relationship.

In some embodiments, fixture 36 provides substantially constrained freedom of translation and/or rotation in one or more degrees of freedom. For example, recess 37 may slightly larger than the cross-section of position marker 42. This permits the position of position marker 42 to be adjusted within recess 37 along axis 62A and/or 64A. Such adjustments may be desirable where the spatial relationship between a position marker constraining fixture, such as fixture 36, and a transducer element array mount, such as mount 38, does not provide a spatial relationship between a position marker and transducer element array that corresponds sufficiently to the reference relationship in the constrained degrees of freedom. For example, such adjustments may be desirable where the probe housing is not manufactured with sufficient precision, or where the fit of a transducer element array in its mount does not determine the location and orientation of the transducer element array with sufficient precision. Where fixture 36 substantially constrains freedom of translation and/or rotation in one or more degrees of freedom, a liquid or gel adhesive, resin or the like can be applied to either or both of fixture 36 and position marker 42 to suspend position marker 42 in fixture 36. Marker 42 can then be positioned in fixture 36 at the location and orientation corresponding to the reference relationship, and held in place until the adhesive has set.

In the embodiment illustrated in FIGS. 2 and 3, probe 32, position base unit 52 and jig 54 are configured so that axis 66A, which corresponds to the degrees of rotational and translational freedom permitted to position marker 42 by fixture 36, is in alignment with reference axis 66B of position base unit 52. Recess 37 is defined in probe 32 so that a feature of position marker 42 that corresponds to a coordinate axis by which its orientation is measured is aligned (or at least substantially aligned) with a reference axis of position base unit 52 when marker 42 is inserted in recess 37. Specifically, axis 66A of recess 37 is aligned with reference axis 66B of position base unit 52, and position marker 42 comprises the feature of cylindrical symmetry about an axis by which its orientation is measured. Provided that position marker 42 fits snugly inside recess 37, the alignment of axes 66A and 66B causes the azimuth and elevation angles of position marker 42 and the location of marker 42 along two of the axes by which position base unit 52 determines the location of position marker 42 to be substantially determined.

This arrangement provides that rotation of position marker 42 about axis 66A (i.e., in its one free degree of rotational freedom) corresponds to rotation about an axis by which its orientation is measured. Alignment of an axis of rotational freedom with an axis by which the position marker's orientation is determined simplifies the use of orientation data from position base unit 52 to place position marker in the reference relationship, since a user rotating of position marker 42 in fixture 36 need only observe changes to one orientation angle measured by position base unit 52. The alignment of axes 66A and 66B also provides correspondence between translation of position marker 42 along axis 66A (i.e., along its one free degree of translational freedom) with translation along reference axis 66B. Alignment of an axis of translational freedom with a reference axis simplifies the use of position data from position base unit 52 to place position marker in the reference relationship, since a user moving position marker 42 in fixture 36 need only observe changes to one location coordinate measured by position base unit 52.

In some embodiments, jig 54 comprises a plurality of seats, each configured to conform to a portion of the housing of a different probe model and to be positioned on jig 54 such that the transducer element arrays inside the different model probes are substantially identically situated with respect to position base unit 52. In some embodiments, seats are configured such that the internal position marker displacement and rotation constraining fixtures are substantially identically situated with respect to position base unit 52. In some such embodiments, seats are configured such that one or more axes of the degrees of freedom permitted by the fixtures are aligned with reference axes of position base unit 52. In embodiments where a reference relationship between a position marker and the transducer element array is defined in terms of a reference location (e.g., X, Y, Z coordinate) and/or a reference orientation (e.g., azimuth, elevation and rotation angles) determined by position base unit 52, identically situating transducer element arrays and position marker constraining fixtures with respect to position base unit 52 using seats matched to probe models allows the same reference location and/or orientation to be used in positioning and/or orienting position markers.

In some embodiments, the seats may be removable and interchangeable. It will be appreciated that other means could be employed to facilitate mounting of probes in jig 54 for uniformly locating and orientating transducer element arrays with respect to position base unit 52. For example, conductive plates could be provided on jig 54 and probe 32 in locations such that when probe 32 is properly mounted on jig 54 an electric current flows across the plates to trigger a signal indicative of proper mounting.

It will be further appreciated that a position marker may be located and oriented in a fixture while the probe is in an unassembled or partially assembled state. For example, a jig for uniformly locating and orientating transducer element arrays with respect to a position base unit may conform to a contour of any part or component of a probe, such as, for example, the fixture, the transducer element array mount, or the like.

Probes comprising internally located position markers, such as probe 32 comprising position marker 42, may provide on or more of the following advantages over probes with removable and/or externally located position markers:

Simplified sterilization of probes. Since marker 42 is internal to probe 32, it is not necessary to sterilize marker 42, or to remove marker 42 in order to sterilize probe 32.

Protection of position markers from physical disturbance. Internally located position marker 42 may be less susceptible to re-orientation and/or repositioning through physical contact than externally located position markers. As a result, position marker 42 may require less frequent re-calibration than externally located markers.

Simplified calibration. The object of calibration is to determine the positional and angular offsets of the position marker and ultrasound image coordinate systems. Because the positional and angular offsets required to calibrate position marker 42 generally do not change, and may be made small by appropriate installation of position marker 42, calibration of position marker 42 may be simpler and faster as compared with externally located position markers.

Simplified cable management. Signal connector 43 of position marker 42 is conveniently routed adjacent signal connector 45 of transducer element array 44. Sleeve 39 tidily encapsulates the pair of signal connectors. As a result, cable management may be simplified as compared with externally located position markers, whose signal connectors may not exit the probe at the same location as the signal connector of a transducer element array.

It will be appreciated that the methods and apparatus disclosed by reference to the example embodiment shown in FIGS. 2 and 3 are susceptible to modification and variation. For, example:

a plurality of position marker constraining fixtures may be provided in a probe;

a plurality of transducer element arrays may be provided in a probe;

a position marker constraining fixture may be rigidly connected to a transducer element array mount via a chassis separate from the probe housing;

a position marker constraining fixture and a transducer element array mount may be formed on a single mounting piece;

etc.

Where a component (e.g. a housing, mount, fixture, transducer element array, position marker, jig, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. The embodiments described herein are only examples. Other example embodiments may be obtained, without limitation, by combining features of the disclosed embodiments.

What is claimed is:

1. A trackable ultrasound probe for use in acquiring ultrasound data, the probe comprising:
    a transducer element array for acquiring the ultrasound image;
    a mount supporting the transducer element array at a fixed location and orientation relative to a housing;
    a position marker enclosed within the housing, the position marker trackable relative to a reference coordinate system by a position sensing system;
    a fixture rigidly connected to the mount, the fixture, including:
    a recess, supporting the position marker and configured to substantially constrain a rotation of the position marker in at least two degrees of rotational freedom about a first axis and a second axis, wherein the first axis and the second axis are perpendicular to each other, and configured to substantially constrain a translational displacement of the position marker along the at least two degrees of translational freedom about the first axis and the second axis, which are perpendicular to each other;
    wherein the orientation of the position marker in the two degrees of rotational freedom determined by the recess and the location of the position marker along the two degrees of translational freedom determined by the recess correspond to a pre-determined reference relationship relative to the transducer element array;
    wherein the position marker rotates along a free degree of the rotational freedom about a third axis, which is different from the first axis and the second axis, to an orientation in the recess, with respect to the transducer element array, based on the pre-determined reference relationship; and
    wherein the position marker translates along a free degree of the translational freedom about a fourth axis, which is different from the first axis and the second axis, to a location in the recess, with respect to the transducer element array, based on the pre-determined reference relationship.

2. The probe according to claim 1 wherein an orientation of the position marker is trackable relative to the reference coordinate system by the position sensing system.

3. The probe according to claim 1, wherein the third and the fourth axes are coincident to each other and both are perpendicular to the first axis and the second axis.

4. The probe according to claim 3, wherein the third axis and the fourth axis are not coincident.

5. The probe according to claim 1 wherein the recess is a substantially cylindrical recess and the mount comprises a substantially rectangular recess and wherein a longitudinal axis of the cylindrical recess is substantially aligned with a mid-point of the rectangular recess.

6. The probe according to claim 1 wherein the position marker comprises a substantially cylindrical body and the transducer element array comprises a substantially linear array of transducer elements and wherein a longitudinal axis of the cylindrical body is substantially aligned with a mid-point of the linear array of transducer elements.

7. The probe according to claim 1 wherein the position marker comprises a substantially cylindrical body and the transducer element array comprises a substantially rectangular array of transducer elements and wherein an axis of the cylindrical body is substantially aligned with a mid-point of the rectangular array of transducer elements.

8. The probe according to claim 1 wherein the fixture comprises a stop, the position marker is against the stop, and wherein the stop is spaced apart from the transducer element array.

9. The probe according to claim 8 wherein the location of the position marker in three degrees of translational freedom is based on a pre-determined reference relationship relative to the transducer element array.

10. A trackable ultrasound probe for use in acquiring ultrasound data, the probe comprising:
    a housing;
    a transducer element array for acquiring ultrasound data, the transducer element array supported at a fixed location and orientation in the housing;
    a fixture including a recess having an end at a pre-determined distance from the transducer element array; and
    a position marker, the entirety of which is translatable and rotatable in the recess of the fixture with respect to the transducer array,
    wherein a position of the marker is trackable relative to a reference coordinate system by a position sensing system, and the position marker is snugly fitted in the recess, whereby an axis by which the orientation of the position marker is measured is aligned with a longitudinal axis of the recess; and
    wherein the housing encloses the position marker.

11. The probe according to claim 10 wherein the recess comprises a cylindrical bore.

12. The probe according to claim 11 wherein an orientation of the position marker is trackable relative to the reference coordinate system by the position sensing system.

13. The probe according to claim 11 wherein the transducer element array is fixed in an opening in the housing.

14. The probe according to claim 11 wherein the transducer element array comprises a substantially linear array of transducer elements and wherein an axis of the bore is substantially aligned with a mid-point of the linear array of transducer elements.

15. The probe according to claim 11 wherein the transducer element array comprises a substantially rectangular array of transducer elements and wherein an axis of the bore is substantially aligned with a mid-point of the rectangular array of transducer elements.

16. The probe according to claim 11 wherein the bore comprises a stop, and wherein the stop is spaced apart from the transducer element array.

17. The probe according to claim 16 wherein the position marker abuts the stop.

18. A trackable ultrasound probe for use in acquiring ultrasound data, the probe comprising:
    a housing;

a transducer element array for acquiring ultrasound data, the transducer element array supported at a fixed location and orientation in the housing;

a fixture supported at a fixed location and orientation in the housing, the fixture comprising a bore having an end at a pre-determined distance from the transducer element array; and a movable position marker entirely moveable within the bore, wherein a position of the moveable position marker in the bore, with respect to the transducer element array, is trackable relative to a reference coordinate system by a position sensing system, wherein the movable position marker is snugly fitted in the bore, wherein an axis by which the orientation of the position marker is measured is aligned with an axis of the bore.

* * * * *